United States Patent
Li et al.

(10) Patent No.: US 9,775,604 B2
(45) Date of Patent: Oct. 3, 2017

(54) SUCTION FIXATION DEVICE AND METHOD

(71) Applicant: Boston Scientific Scimed, Inc., Maple Grove, MN (US)

(72) Inventors: Jamie Li, Lexington, MA (US); Leo James Lichte, Riverside, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 402 days.

(21) Appl. No.: 14/332,102

(22) Filed: Jul. 15, 2014

(65) Prior Publication Data

US 2015/0045817 A1 Feb. 12, 2015

Related U.S. Application Data

(60) Provisional application No. 61/864,340, filed on Aug. 9, 2013.

(51) Int. Cl.
| | |
|---|---|
| *A61B 17/04* | (2006.01) |
| *A61F 2/00* | (2006.01) |
| *A61B 17/00* | (2006.01) |
| *A61B 17/30* | (2006.01) |

(52) U.S. Cl.
CPC ...... *A61B 17/0482* (2013.01); *A61B 17/0469* (2013.01); *A61B 2017/00805* (2013.01); *A61B 2017/306* (2013.01); *A61F 2/0045* (2013.01)

(58) Field of Classification Search
CPC ............ A61B 17/0482; A61B 17/0469; A61B 2017/306
USPC ......... 606/108, 46, 139, 142, 144, 148, 151, 606/153, 190
See application file for complete search history.

(56) References Cited

U.S. PATENT DOCUMENTS

| | | | | |
|---|---|---|---|---|
| 5,184,515 | A * | 2/1993 | Terry | G01L 1/18 338/4 |
| 5,792,153 | A * | 8/1998 | Swain | A61B 17/0469 112/169 |
| 7,175,636 | B2 * | 2/2007 | Yamamoto | A61B 17/0469 606/139 |
| 8,152,821 | B2 * | 4/2012 | Gambale | A61B 17/00234 606/139 |

* cited by examiner

*Primary Examiner* — Vy Bui
(74) *Attorney, Agent, or Firm* — Brake Hughes Bellermann LLP

(57) ABSTRACT

In one embodiment, a medical device includes a tissue suction housing and a moveable member disposed in the tissue suction housing. The tissue suction housing has a proximal end and a distal end. The distal end has an opening and the tissue suction housing has at least two suturing device openings. The tissue suction housing is configured to pull up bodily tissue through the opening in the distal end when placed under a vacuum and to receive a suturing device through one of the suturing device openings.

19 Claims, 5 Drawing Sheets

SUCTION FIXATION DEVICE AND METHOD

CROSS-REFERENCE TO RELATED APPLICATION

This application is a Nonprovisional of, and claims priority to, U.S. Patent Application No. 61/864,340, filed on Aug. 9, 2013, entitled "SUCTION FIXATION DEVICE AND METHOD", which is incorporated by reference herein in its entirety.

TECHNICAL FIELD

This disclosure relates generally to medical devices and more particularly to medical devices that include a suction fixation device and related techniques.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures include placing a support member or implant into the body of the patient such that the support member or implant provides support to a portion of the body of the patient. Specifically, in some medical procedures, the support member or implant may be fixed or coupled to the body of the patient at various locations within the body of the patient and a support portion of the support member or implant may be placed beneath the portion of the body to be supported. For instance, a patch of prosthetic material, such as a mesh material, may be attached to a layer (e.g., a thin layer) of tissues in the body of the patient such as a wall of an organ, for example, the vaginal wall. In some cases, a second portion of the mesh material may be attached to a layer of muscle or ligament on top of a bone such as, for example, the sacrum.

In some known medical procedures, fixation devices are used fix or couple portions of the support member to portions of the body of the patient. A need exists for fixation devices that effectively retain a support member in place within a body of a patient and control a depth of penetration of the devices. A need also exists for a tool for effectively placing such fixation devices inside the body of the patient.

SUMMARY

In one general aspect, a medical device includes a tissue suction housing and a moveable member disposed in the tissue suction housing. The tissue suction housing has a proximal end and a distal end. The distal end has an opening and the tissue suction housing has at least two suturing device openings. The tissue suction housing is configured to pull up bodily tissue through the opening in the distal end when placed under a vacuum and to receive a suturing device through one of the suturing device openings.

In another general aspect, a medical device includes a tissue suction housing and a moveable member disposed in the tissue suction housing. The tissue suction housing has a proximal end and a distal end. The distal end has an opening and the tissue suction housing has at least two suturing device openings. A position of the moveable member is adjustable along an inner surface of the tissue suction housing. The tissue suction housing is configured to pull up bodily tissue through the opening in the distal end when placed under a vacuum and the position of the moveable member defines a depth of penetration into the bodily tissue by a suturing device received through one of the suturing device openings.

In another general aspect, a method of suturing bodily tissue within a body of a patient includes (1) inserting a medical device within the body of the patient, the medical device includes a tissue suction housing having at least two suturing device openings, an opening at a distal end of the tissue suction housing and a moveable member disposed in the tissue suction housing, (2) placing a vacuum on the tissue suction housing to pull up the bodily tissue through the opening at the distal end of the tissue suction housing, and (3) inserting a suturing device through one of the suturing device openings to pass a suture through the bodily tissue.

DETAILED DESCRIPTION

Figure 1A:
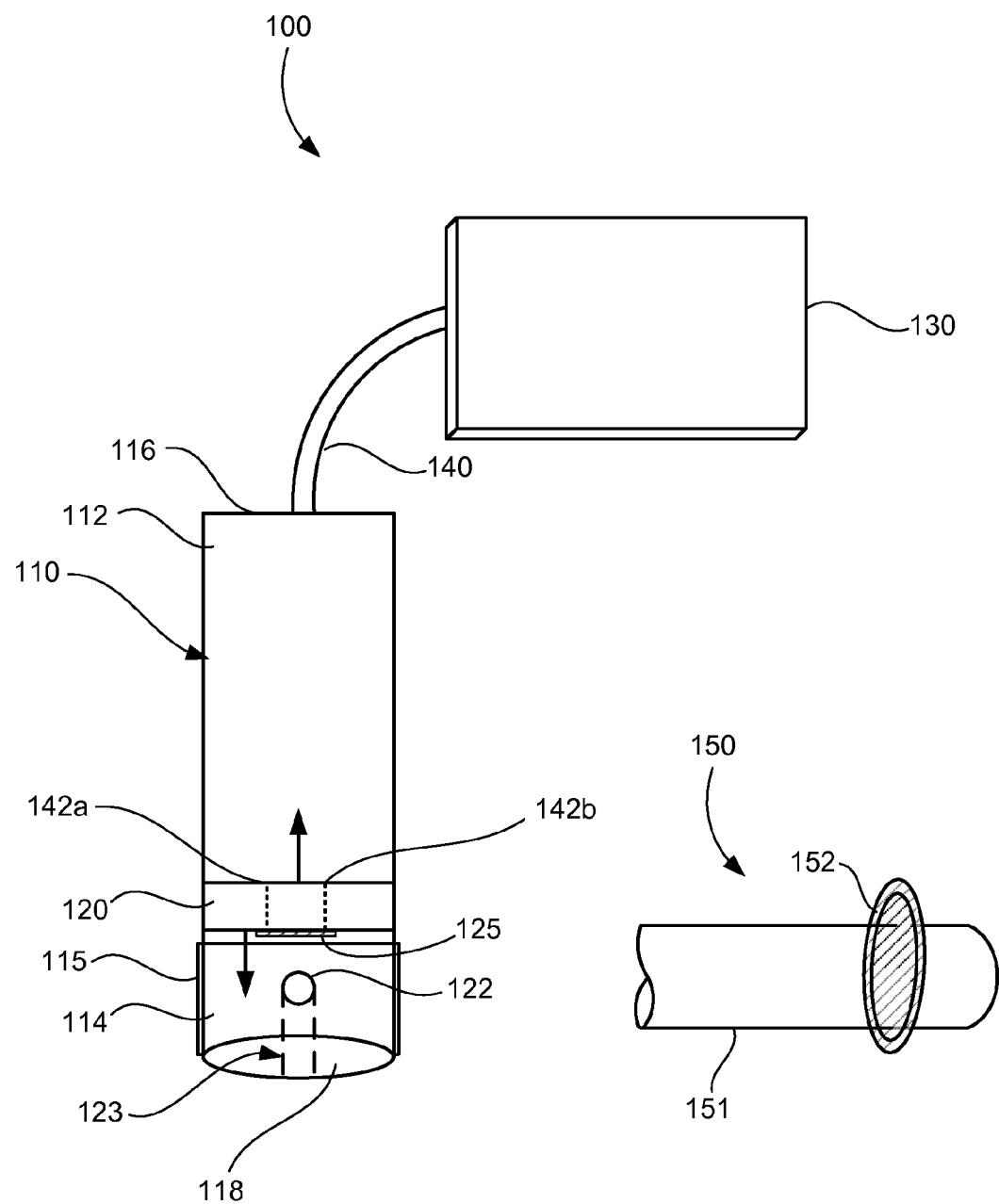
FIG. 1A is a schematic illustration of an apparatus according to an embodiment of the invention.

The devices and methods described herein are generally directed to procedures for suturing implants within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured or coupled to a vaginal wall.

In another embodiment, an implant can be secured through a laparoscopic and/or a transvaginal approach. The devices and methods described herein may be used to complete the mesh fixation process to vaginal tissue.

In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved.

Various fixation devices and methods are described for delivering and securing an implant within the body of the patient. The implants, fixation devices, delivery devices, and procedures described herein may be used in a female patient or a male patient.

An implant according to an embodiment of the invention can be implanted, for example, through an abdominal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision. For example, a procedure may include an abdominal incision to secure or couple an implant to a vaginal wall.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

FIG. 1A is a schematic illustration of an apparatus or medical device 100 according to an embodiment of the invention. The apparatus or medical device 100 includes a tissue suction housing 110, a movable member 120 and a vacuum member 130. The vacuum member 130 may be connected to the tissue suction housing 110 by a tube member 140.

The apparatus 100 is configured to be inserted into a body of a patient such that at least a portion of the apparatus 100 is disposed within the body of the patient. In some embodiments, the apparatus 100 may be inserted into the body of the patient either through a laparoscopic port or transvaginal. As will be discussed in more detail below, the apparatus is configured to be placed adjacent a desired coupling or fixation location within the body.

The tissue suction housing 110 includes a first end portion 112 (or proximal end) and a second end portion 114 (or a distal end). In some embodiments, the tissue suction housing 110 defines an opening 116 at the first end portion 112 and an opening 118 at the second end portion 114. The opening 116 provides a connection point for coupling the tube member 140 between the tissue suction housing 110 and the vacuum member 130. The opening 116 may be closed and sealed to provide the vacuum in the tissue suction housing 110 from the vacuum member 130 through the tube member 140.

The tissue suction housing 110 includes at least two suturing device openings 122. The suturing device openings 122 may pass through one side of the tissue suction housing 110 to an opposite side of the tissue suction housing 110. In this manner, a suturing device (not shown) may be passed through the tissue suction housing 110 using the suturing device openings 122. That is, the suturing device may enter one side of the tissue suction housing 110 through one of the suturing device openings 122, pass through the tissue suction housing 110 and exit the an opposite side of the tissue suction housing 110. The one suturing device opening 122 may have a corresponding suturing device opening (not shown) on the opposite side of the tissue suction housing 110 through which the suturing device exits.

The suturing device openings 122 each may include a slot 123. The slot 123 may be an opening that extends from the suturing device openings 122 to the opening 118. The slot 123 is configured to provide an escape port for a suturing device that is being passed through the suturing device openings 122 through the tissue suction housing 110.

In some embodiments, the suturing device may be a needle. In other embodiments, the suturing device may be a pin. For example, the pin may be a biodegradable pin. In other examples, the pin may be a polymeric pin.

The tissue suction housing 110 is configured to be placed adjacent a location in the body and to draw a suction on bodily tissue. The tissue suction housing 110 is configured to draw a suction to pull a portion of bodily tissue into the tissue suction housing 110 through the opening 118 at the second end portion 114. The vacuum member 130 is configured to place a vacuum on the tissue suction housing 110 through the tube member 140. The vacuum creates a suction force at the opening 118. The suction force is sufficient to pull the portion of the bodily tissue and any bodily implant material overlaying the tissue into the tissue suction housing 110.

In some example embodiments, the apparatus 100 includes a sleeve 115. The sleeve 115 may fit around the suction tissue housing 110 near the distal end 114. The sleeve 115 may slidably move along the outside surface of the tissue suction housing 110. The sleeve 115 may be configured in a first position to cover the suturing device openings 122 and the slots 123 to block the openings and the slots to assist creating the vacuum to pull up the bodily tissue. The sleeve 115 may be configured to slide to a second position to uncover the suturing device openings 122 and the slots 123 to unblock the openings and the slots after the bodily tissue has been pulled up to allow a suturing device to pass through the tissue suction housing 110 and the bodily tissue.

In other example embodiments, the sleeve 115 may include matching suturing device openings and slots. The sleeve 115 may be configured to rotate about the distal end 114 of the tissue suction housing 110. The sleeve 115 may be rotated to a first position that covers the suturing device openings 122 and the slots 123 during creation of the vacuum. Then, the sleeve 115 may be rotated to a second position that aligns the openings and slots on the sleeve 115 with the suturing device openings 122 and slots 123 to allow a suturing device to pass through the tissue suction housing 110 and the bodily tissue.

In some embodiments, the sleeve 115 may be a plastic tube. The plastic tube may be transparent. In other embodiments, the sleeve 115 may be made from other materials. For example, in other embodiments, the sleeve 115 may be a plastic sheet that covers the suturing device openings 122 and slots 123 and through which the suturing device may pass directly through the sheet.

The tissue suction housing 110 is configured to pull the bodily tissue and any overlaying implant material through the opening 118 past the suturing device openings 122. A suturing device, including any attached suturing material, may be passed through the suturing device openings 122 through the bodily tissue and any overlaying implant material to fasten the implant material to the tissue. The suturing device may exit an opposite side of through the other suturing device opening 122.

After the suturing device and suturing material have fastened the implant to the tissue, the vacuum may be released by the vacuum member 130 and the suction force is terminated. When the suction force is terminated, the tissue and implant are released from the tissue suction housing 110 back through the opening 118. The sleeve 115 may be re-positioned (e.g., slid or rotated) so that the suturing device openings 122 and the slots 123 are covered and ready for the next cycle of fixation.

In some embodiments, when the tissue is vaginal tissue, the apparatus 100 may be used with a separate vaginal manipulation member 150. The vaginal manipulation member 150 may include an elongate member 151 and a protrusion member 152. The elongate member 150 may be an elongate tube and the protrusion member 152 may be disposed around at least a portion of the outer surface of the elongate member 150. In other embodiments, the vaginal manipulation member 150 may have a different shape.

The vaginal manipulation member 150 may be a component that is separate from the apparatus 100, but may be used as part of the process of using the apparatus 100 to suture vaginal tissue or to fasten an implant to vaginal tissue. The apparatus 100 may be placed adjacent vaginal tissue and the vaginal manipulation member 150 may be used to assist pushing the vaginal tissue into the opening 118 as the vacuum is being applied to the tissue suction housing 110.

In one example embodiment, the suturing device may enter the suturing device openings 122 and pass through the tissue suction housing 110 such that the suturing device is perpendicular to the tissue suction housing 110. In other example embodiments, a suturing device opening on the opposite side of the suturing device opening 122 may not be directly in-line with the suturing device opening 122, in which case, the suturing device may not be perpendicular to the tissue suction housing 110.

The device 100 is configured to control a depth of penetration of the suturing device and the suturing material into the bodily tissue. In one embodiment, the movable member 120 in the tissue suction housing 110 is used to control the depth of penetration into the bodily tissue. The movable member 120 is configured to be movable within the tissue suction housing 110. For example, the movable member 120 may be movable through a handle (not shown). The movable member 120 may be moved within the tissue suction housing 110 along a length of the tissue suction housing 110. The moveable member 120 may traverse along the inside surface of the tissue suction housing 110 from the first end portion 112 to the second end portion 114. The moveable member 120 may be fixed in position at any point along the inside surface of the tissue suction housing 110. The moveable member 120 may be fixed in position above the suturing device openings 122 to enable the bodily tissue and implant material to be drawn in above the suturing device openings 122 to allow for passage of the suturing device through the tissue.

The movable member 120 may be configured to move transverse a distance between 1 mm and 10 mm. In some embodiments, the movable member 120 may be configured to transverse a distance between 2 mm and 5 mm. In some embodiments, the distance of traversal may be measured from the opening 118 towards the proximal end 112 away from the distal end 114.

The depth of penetration is determined by the placement of the moveable member 120 within the tissue suction housing 110. A deeper depth of penetration is achieved when the movable member 120 is fixed in position farther from the second end portion 114 and closer to the first end portion 112. Less depth of penetration is achieved when the moveable member 120 is fixed in position closer to the second end portion 114.

In this manner, the device 100 may be used in different places within the body that may have different fastening requirements in terms of desired depth of penetration into the tissue. For tissue that requires a lesser depth of penetration, the device 100 may be configured by positioning the moveable member 120 closer to the second end portion 114. For tissue that requires a deeper depth of penetration, the device 100 may be configured by positioning the moveable member 120 closer to the first end portion 112.

In some embodiments, the device 100 may be adjusted for depths of penetration into tissue between about 1 mm and 10 mm by adjusting the moveable member 120. For example, the depths of penetration may include ranges between about 2 mm and 10 mm, 2 mm and 7 mm and 2 mm and 5 mm. In other embodiments, other depths of penetration into tissue may be realized, including depths of less than 1 mm.

In some embodiments, the moveable member 120 enables the device 100 to draw in (or suck up) more tissue than a device having a larger size opening at a distal end of a housing. In this manner, a size (or diameter) of the opening 118 may be smaller than other devices, yet the device 100 is capable of drawing in more tissue. Thus, an overall width of the device 100, as measured from one side of the tissue suction housing 110 to an opposite side of the tissue suction housing 110, may be made smaller, but still be capable of suturing an implant to a larger tissue area than other wider and larger devices.

The moveable member 120 may include one or more holes 142a and 142b. The holes 142a and 142b are configured to enable the vacuum member 130 to place a vacuum in the tissue suction housing 110 through the moveable member 120. In this manner, the suction force is applied through the tissue suction housing 110, including the moveable member 120 through the holes 142a and 142b, and works to draw the tissue into the tissue suction housing 110 through the opening 118.

In some embodiments, the moveable member 120 may not be a flat member. For example, the moveable member 120 may be concave-shaped or convex-shaped. In this manner, a concave-shaped member or convex-shaped member may allow contact with tissue, but it may not completely block the vacuum around the edges.

The tissue suction housing 110 may be implemented in different shapes. In one example embodiment, the tissue suction housing 110 may be tubular or cylindrical in shape. In other example embodiments, the tissue suction housing 110 may be other shapes including, but not limited to, square, rectangular, triangular, or other shapes.

For example, in some embodiments, the tissue suction housing 110 or at least the distal end 114 of the tissue suction housing 110 may be shaped like a rectangle. A rectangle-shaped distal end 114 may vacuum up less tissue than other-shaped housings, but the rectangle ends may be aligned with the direction of the suturing device.

In some embodiments, the distal end 114 of the tissue suction housing 110 may be made of a softer material than the rest of the tissue suction housing 110 to assist in sealing the vacuum against the bodily tissue. In some embodiments, the distal end 114 may include a separate component seal or the most distal end may be softer than the rest of the distal end.

In use, the apparatus 100 may then be inserted into a body of a patient. For example, in some implementations, the apparatus 100 may be inserted into a body of a patient through an abdominal incision. In other implementations, the apparatus 100 may be inserted into a body of a patient through a vaginal or other bodily incision. An end portion, such as the second end portion 114 (a distal end portion) of the tissue suction housing 110 may be disposed adjacent to the bodily tissue into which a suturing device and suturing material is to be inserted. In some embodiments, a bodily implant, such as a mesh type bodily implant or a lead, may be disposed between the second end portion 114 of the tissue suction housing 110 and the tissue.

The moveable member 120 may be positioned at a desired location within the tissue suction housing 110 by traversing the moveable member 120 along the inner tissue suction housing 110 to the desired location. The moveable member 120 may be set or fixed in the desired location, where the desired location relates to a desired depth of penetration of the suturing device into the tissue. A vacuum may be applied to the tissue suction housing 110 using the vacuum member 130 and the tube member 140 to apply a suction to pull up the tissue and any overlaying implant through the opening 118 into the tissue suction housing 110 past the suturing device openings 122 until the tissue contacts the moveable member 120. The moveable member 120 is configured to act as a stop to prevent the tissue from being pulled further into the tissue suction housing 110. The moveable member 120 causes the tissue to stop at the desired location at the desired depth of penetration. The suturing device and any suturing material may be threaded through the tissue to suture the tissue and/or to fasten any implant to the tissue. The vacuum may be released, which releases the tissue from the tissue suction housing 110. The device 100 may then be repositioned within the body of the patient to suture or fasten another portion of tissue.

In some embodiments, the device 100 may include one or more sensors 125. The sensors 125 may be disposed on the moveable member 120 on a side facing towards the opening 118. The sensors 125 may be configured to sense when the tissue and/or implant comes into contact with the moveable member 120. The sensors 125 may provide an indication of contact with the moveable member 120 and that the tissue is in position for suturing or fastening. In this manner, when an indication is received from the sensors 125, an operator of the device 100 may be made aware that the tissue and/or implant are in the desired position.

In some embodiments, the sensors 125 may include thermocouples formed by conjoined wires. When the vacuumed tissue contacts an intersection point of the thermocouple wires, a controller may display a change in temperature at the level of the moveable member 120 to provide an indication of the tissue contact with the movable member 120.

In some embodiments, more than one suturing device may be inserted at a same time. Multiple suturing devices may be inserted vertically and/or around the circumference of the device. The distal end 114 of the tissue suction housing 110 may include multiple slots to accommodate a single suturing device from many directions and/or allow multiple suturing devices from multiple directions.

Figure 1B:
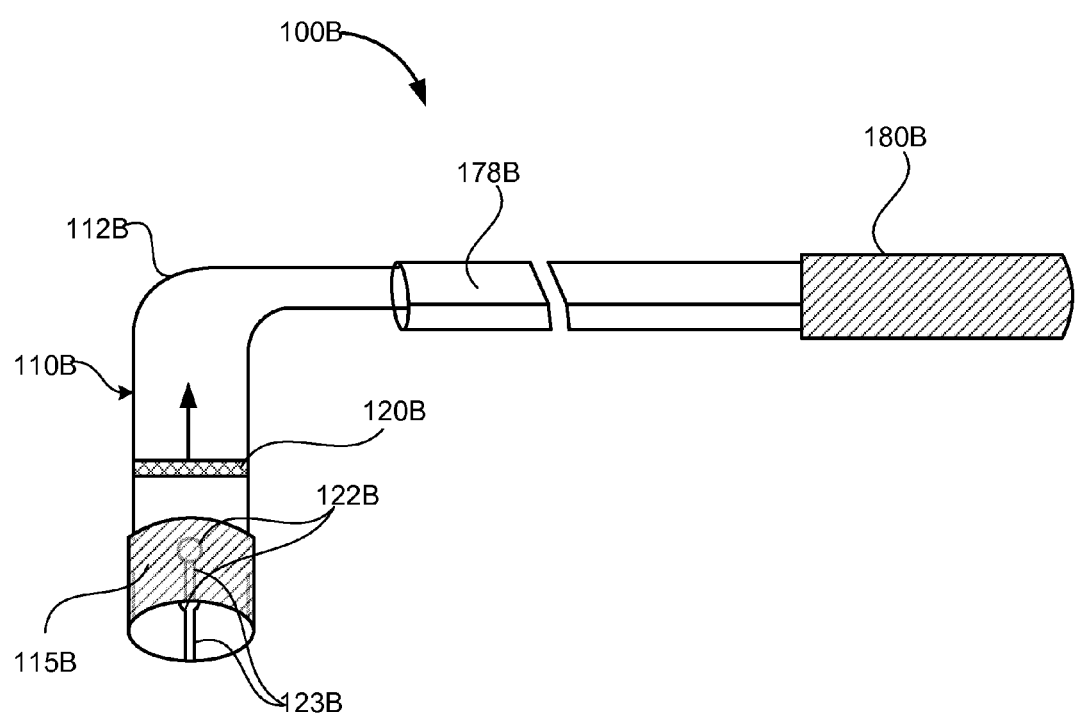
FIG. 1B is a schematic illustration of an apparatus according to an embodiment of the invention.

FIG. 1B illustrates an example embodiment of a device 100B. In the illustrated embodiment of FIG. 1B, the device 100B may include some or all of the features described above with respect to the device 100 described with respect to FIG. 1A. In this illustrated example of FIG. 1B, the device 100B includes a tissue suction housing 110B and a movable member 120B. The tissue suction housing includes suturing device openings 122B and slots 123B. In some embodiments, the device 100B may include a sleeve 115B, as described above with respect to sleeve 115 of FIG. 1A.

In this example embodiment of FIG. 1B, the proximal end 112B of the tissue suction housing 110B may curve at an angle (e.g., a right angle or some other angle). The device 100B may include a handle 180B that connects to the proximal end 112B of the tissue suction housing 110B through a handle connector 178B. The handle connector 178B may be an elongate member that is disposed between the tissue suction housing 110B and the handle 180B.

The handle 180B may be configured to control and manipulate the device 100B. In some embodiments, the handle 180B may be configured to control the vacuum force applied to the suction tissue housing 110B. The handle 180B may be configured to control the movement of the moveable member 120B, including fixing the moveable member 120B in position such that a desired depth of penetration is achieved. The handle 180B may include a suturing device controls to control the suturing device such that the device 100B may be used to make multiple suturing device passes through the tissue and/or implant.

Figure 2:
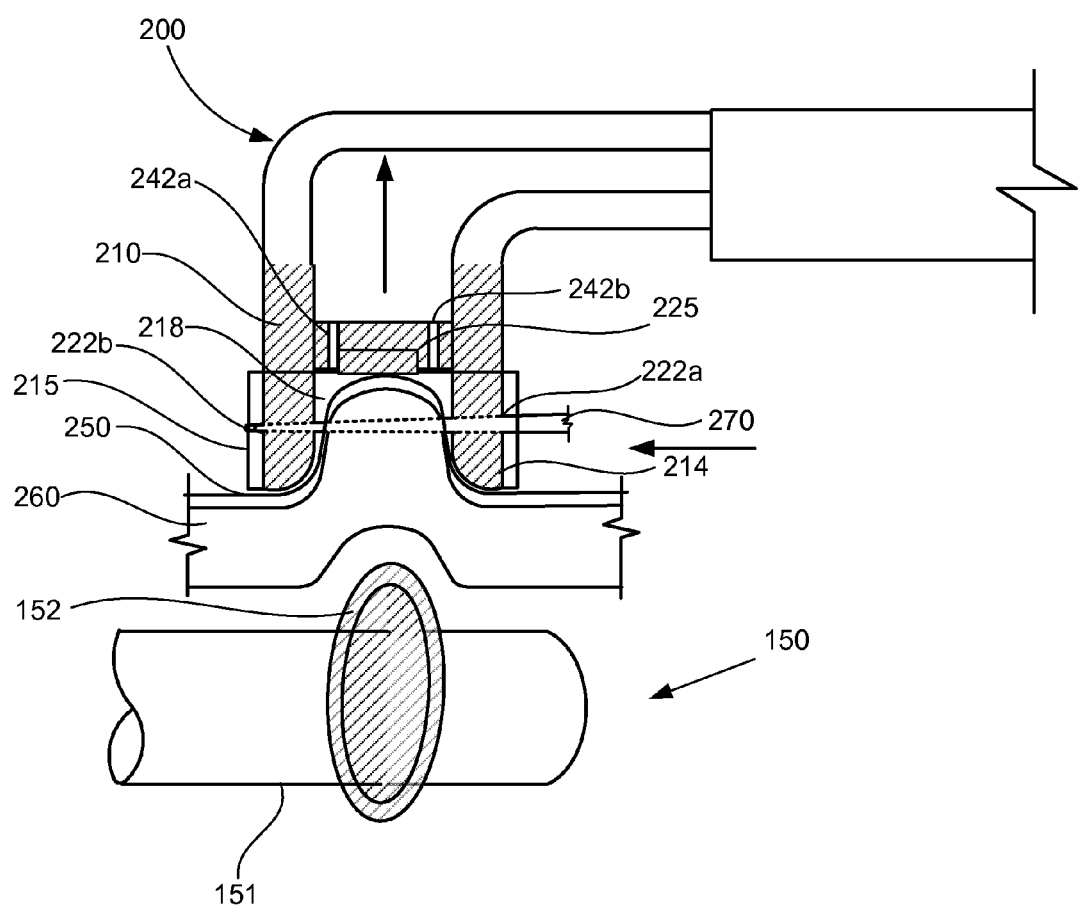
FIG. 2 is a partial break away view of a fixation device according to an embodiment of the invention.

FIG. 2 illustrates a partial break away view of an apparatus 200 at a distal end 214 of the apparatus according to an example embodiment. The apparatus 200 is engaged with a bodily implant 250. The apparatus 200 may include some or all of the features of the devices 100 and 100B described above with respect to FIGS. 1A and 1B, respectively.

The apparatus 200 is configured to be inserted into a body of a patient such that at least a portion of the apparatus 200 is disposed within the body of the patient. In some embodiments, the apparatus 200 may be inserted into the body of the patient either through a laparoscopic port or transvaginally. As will be discussed in more detail below, the apparatus is configured to be placed adjacent a desired coupling or fixation location within the body.

The apparatus 200 includes a tissue suction housing 210 and a moveable member 220. The tissue suction housing 210 defines an opening 218 at the second end portion 214. The tissue suction housing 210 includes two suturing device openings 222a and 222b. The suturing device openings 222a, 222b may pass through one side of the tissue suction housing 210 to an opposite side of the tissue suction housing 210. In this manner, a suturing device 270 may be passed through the tissue suction housing 210 using the suturing device openings 222a and 222b. That is, the suturing device 270 may enter one side of the tissue suction housing 210 through the suturing device opening 222a, pass through the tissue suction housing 210 and exit the an opposite side of the tissue suction housing 210 through the suturing device opening 222b. The suturing device openings 222a and 222b each may include a slot (not shown), as described above with respect to the slots 123 and 123B of FIGS. 1A and 1B, respectively.

The tissue suction housing 210 is configured to be placed adjacent a location in the body and to draw a suction on bodily tissue 260. The tissue suction housing 210 is configured to draw a suction to pull a portion of bodily tissue 260 into the tissue suction housing 210 through the opening 218 at the second end portion 214. The vacuum member (not shown in FIG. 2) is configured to place a vacuum on the tissue suction housing 210 through the tube member (not shown in FIG. 2). The vacuum creates a suction force at the opening 218. The suction force is sufficient to pull the portion of the bodily tissue 260 and any bodily implant material 250 overlaying the tissue 260 into the tissue suction housing 210.

In some example embodiments, the apparatus 200 includes a sleeve 215. The sleeve 215 may fit around the suction tissue housing 210 near the distal end 214. The sleeve 215 may slidably move along the outside surface of the tissue suction housing 210. The sleeve 215 may be configured in a first position to cover the suturing device openings 222a and 222b and the slots to block the openings and the slots to assist creating the vacuum to pull up the bodily tissue. The sleeve 215 may be configured to slide to a second position to uncover the suturing device openings 222a and 222b and the slots to unblock the openings and the slots after the bodily tissue has been pulled up to allow a suturing device to pass through the tissue suction housing 210 and the bodily tissue.

In other example embodiments, the sleeve 215 may include matching suturing device openings and slots. The sleeve 215 may be configured to rotate about the distal end 214 of the tissue suction housing 210. The sleeve 215 may be rotated to a first position that covers the suturing device openings 222a and 222b and the slots during creation of the vacuum. Then, the sleeve 215 may be rotated to a second position that aligns the openings and slots on the sleeve 215 with the suturing device openings 222a and 222b and slots to allow a suturing device to pass through the tissue suction housing 210 and the bodily tissue.

In some embodiments, the sleeve 215 may be a plastic tube. The plastic tube may be transparent. In other embodiments, the sleeve 215 may be made from other materials. For example, in other embodiments, the sleeve 215 may be a plastic sheet that covers the suturing device openings 222a and 222b and slots and through which the suturing device may pass directly through the sheet.

The tissue suction housing 210 is configured to pull the bodily tissue 260 and any overlaying implant material 250 through the opening 218 past the suturing device openings 222a and 222b. A suturing device 270, including any attached suturing material, may be passed through the suture device opening 222a through the bodily tissue 260 and any overlaying implant material 250 to fasten the implant material 250 to the tissue 260. The suturing device 270 may exit an opposite side through the suturing device opening 222b.

After the suturing device 270 and suturing material have fastened the implant 250 to the tissue 260, the vacuum may be released by the vacuum member and the suction force is terminated. When the suction force is terminated, the tissue 260 and implant 250 are released from the tissue suction housing 210 back through the opening 218. The sleeve 215 may be re-positioned (e.g., slid or rotated) so that the suturing device openings 222a and 222b and the slots are covered and ready for the next cycle of fixation.

As described above with respect to FIG. 1A, the device 200 may use a vaginal manipulator member 150 when the device 200 is being used to suture or fix an implant to vaginal tissue.

In one example embodiment, the suturing device 270 may enter the suturing device openings 222a and 222b and pass through the tissue suction housing 210 such that the suturing device 270 is perpendicular to the tissue suction housing 210. In other example embodiments, a suturing device opening on the opposite side of the suturing device opening 222a may not be directly in-line with the suturing device opening 222a, in which case, the suturing device 270 may not be perpendicular to the tissue suction housing 210.

The device 200 is configured to control a depth of penetration of the suturing device 270 and the suturing material into the bodily tissue 260. In one embodiment, the movable member 220 in the tissue suction housing 210 is used to control the depth of penetration into the bodily tissue 260. The movable member 220 is configured to be movable within the tissue suction housing 210. The movable member 220 may be moved within the tissue suction housing 210 along a length of the tissue suction housing 210. The moveable member 220 may traverse along the inside surface of the tissue suction housing 210 from the first end portion to the second end portion 214. The moveable member 220 may be fixed in position at any point along the inside surface of the tissue suction housing 210. The moveable member 220 may be fixed in position above the suturing device openings 222a and 222b to enable the bodily tissue 260 and implant material 250 to be drawn in above the suturing device openings 222a and 222b to allow for passage of the suturing device 270 through the tissue 260.

The movable member 220 may be configured to move transverse a distance between 1 mm and 10 mm. In some embodiments, the movable member 220 may be configured to transverse a distance between 2 mm and 5 mm. In some embodiments, the distance of traversal may be measured from the opening 218 towards the proximal end away from the distal end 214.

The depth of penetration is determined by the placement of the moveable member 220 within the tissue suction housing 210. A deeper depth of penetration is achieved when the movable member 220 is fixed in position farther from the second end portion 214 and closer to the first end portion. Less depth of penetration is achieved when the moveable member 220 is fixed in position closer to the second end portion 214.

In this manner, the device 200 may be used in different places within the body that may have different fastening requirements in terms of desired depth of penetration into the tissue. For tissue that requires a lesser depth of penetration, the device 200 may be configured by positioning the moveable member 220 closer to the second end portion 214. For tissue that requires a deeper depth of penetration, the device 200 may be configured by positioning the moveable member 220 closer to the first end portion.

In some embodiments, the device 200 may be adjusted for depths of penetration into tissue between about 1 mm and 10 mm by adjusting the moveable member 220. For example, the depths of penetration may include ranges between about 2 mm and 10 mm, 2 mm and 7 mm, and 2 mm and 5 mm In other embodiments, other depths of penetration into tissue may be realized, including depths of less than 1 mm.

In some embodiments, the moveable member 220 enables the device 200 to draw in (or suck up) more tissue than a device having a larger size opening at a distal end of a housing. In this manner, a size (or diameter) of the opening 218 may be smaller than other devices, yet the device 200 is capable of drawing in more tissue. Thus, an overall width of the device 200, as measured from one side of the tissue suction housing 210 to an opposite side of the tissue suction housing 210, may be made smaller, but still be capable of suturing an implant to a larger tissue area than other wider and larger devices.

The moveable member 220 may include one or more holes 242a and 242b. The holes 242a and 242b are configured to enable the vacuum member to place a vacuum in the tissue suction housing 210 through the moveable member 220. In this manner, the suction force is applied through the tissue suction housing 210, including the moveable member 220 through the holes 242a and 242b, and works to draw the tissue 260 into the tissue suction housing 210 through the opening 218.

The tissue suction housing 210 may be implemented in different shapes. In one example embodiment, the tissue suction housing 210 may be tubular or cylindrical in shape. In other example embodiments, the tissue suction housing 210 may be other shapes including, but not limited to, square, rectangular, triangular, or other shapes.

In use, the apparatus 200 may then be inserted into a body of a patient. For example, in some implementations, the apparatus 200 may be inserted into a body of a patient through an abdominal incision. In other implementations, the apparatus 200 may be inserted into a body of a patient through a vaginal or other bodily incision. An end portion, such as the second end portion 214 (a distal end portion) of the tissue suction housing 210 may be disposed adjacent to the bodily tissue 260 into which a suturing device and suturing material is to be inserted. In some embodiments, a bodily implant 250, such as a mesh type bodily implant or a lead, may be disposed between the second end portion 214 of the tissue suction housing 210 and the tissue 260.

The moveable member 220 may be positioned at a desired location within the tissue suction housing 210 by traversing the moveable member 220 along the inner tissue suction housing 210 to the desired location. The moveable member 220 may be set or fixed in the desired location, where the desired location relates to a desired depth of penetration of the suturing device into the tissue 260. A vacuum may be applied to the tissue suction housing 210 using the vacuum member and the tube member to apply a suction to pull up the tissue 260 and any overlaying implant 250 through the opening 218 into the tissue suction housing 210 past the suturing device openings 222a and 222b until the implant 250 and tissue 260 contact the moveable member 220. The moveable member 220 is configured to act as a stop to prevent the tissue 260 from being pulled further into the tissue suction housing 210. The moveable member 220 causes the tissue 260 to stop at the desired location at the desired depth of penetration. The suturing device 270 and any suturing material may be threaded through the tissue 260 to suture the tissue and/or to fasten the implant 250 to the tissue 260. The vacuum may be released, which releases the tissue 260 from the tissue suction housing 210. The device 200 may then be repositioned within the body of the patient to suture or fasten another portion of tissue.

In some embodiments, the device 200 may include one or more sensors 225. The sensors 225 may be disposed on the moveable member 220 on a side facing towards the opening 218. The sensors 225 may be configured to sense when the tissue 260 and/or implant 250 comes into contact with the moveable member 220. The sensors 225 may provide an indication of contact with the moveable member 220 and that the tissue is in position for suturing or fastening. In this manner, when an indication is received from the sensors 225, an operator of the device 200 may be made aware that the tissue 260 and/or implant 250 are in the desired position.

In some embodiments, the suturing device may be at least partially curved. In some instances, the suturing device is curved to generally follow around at least a portion of the circumference of the distal end 214 of the tissue suction housing 210.

In the illustrated example, the suturing device 270 is a needle. In other embodiments, the suturing device may be a fastener, such as a pin. In some examples, the fastener may be designed to remain in place following release of the vacuum. Such a fastener may further be designed to remain is position permanently or biodegrade. For example, the pin may be a biodegradable pin. If the fastener is permanent, then it may be designed to become flexible due to, for example, time and/or partial biodegradation. In other examples, the pin may be a polymeric pin. In other embodiments, the suturing device 270 may be other types of devices that are configured to suture tissue and/or to fasten implants to the tissue.

Figure 3:
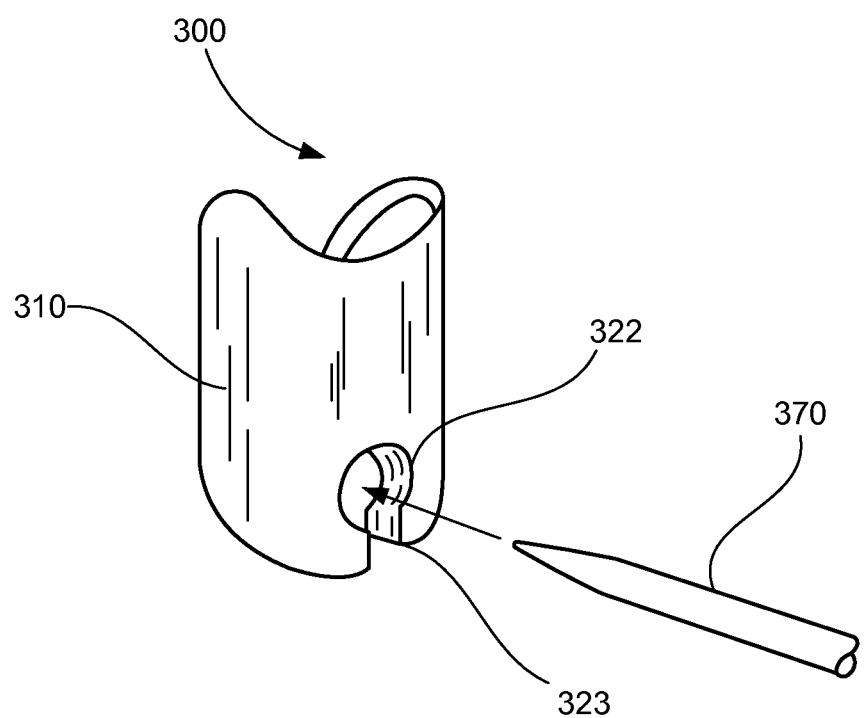
FIG. 3 is a perspective view of a tissue suction housing according to an embodiment of the invention.

FIG. 3. illustrates an example tissue suction housing 310 according to an example embodiment. The tissue suction housing 310 may include the same or similar features as the tissue suction housings 110, 110B and 210 of FIGS. 1A, 1B and 2, respectively.

In the illustrated embodiment, the tissue suction housing 310 is a tubular or cylindrical in shape. As discussed above with respect to FIGS. 1A, 1B and 2, the tissue suction housing 310 includes suturing device openings 322 for receiving a suturing device 370. In this example, the suturing device opening 322 may be at the very distal end of the tissue suction housing 310 and include a slot 323 at the bottom portion of the opening 322. In the illustrated embodiment, the suturing device 370 is a needle. As discussed above, in other embodiments, other types of suturing devices may be used and the suturing device opening 322 may be shaped in a different manner to accommodate a different type or differently shaped suturing device.

Figure 4:
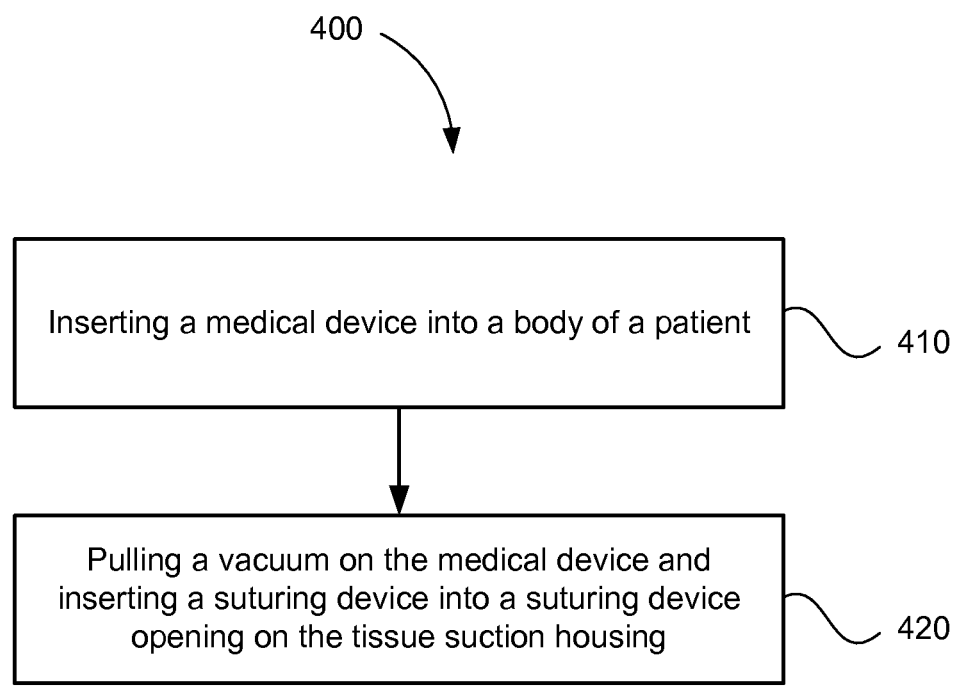
FIG. 4 is a flow chart of a method of suturing bodily tissue according to an embodiment of the invention.

FIG. 4 is a flow chart of a method 400 of suturing bodily tissue according to an embodiment of the invention. At 410, a medical device is inserted into a body of the patient. In some embodiments, the medical device includes a tissue suction housing having a moveable member and a suturing device opening. At 420, a vacuum is placed on the tissue suction housing to pull up the tissue into an opening of the tissue suction housing and a suturing device is inserted through the suturing device opening into the tissue.

The moveable member may be adjusted or moved within the tissue suction housing to allow for different depths of penetration into the bodily tissue. The moveable member acts as a stop or block to suture only to the desired depth of penetration. The medical device may be used to suture tissue and/or to fasten a bodily implant to the tissue.

In one embodiment, a medical device includes a tissue suction housing and a moveable member disposed in the tissue suction housing. The tissue suction housing has a proximal end and a distal end. The distal end has an opening and the tissue suction housing has at least two suturing device openings. The tissue suction housing is configured to pull up bodily tissue through the opening in the distal end when placed under a vacuum and to receive a suturing device through one of the suturing device openings.

In some embodiments, the tissue suction housing is tubular shaped.

In some embodiments, the tissue suction housing is configured to pull up the bodily tissue and an implant disposed on the bodily tissue to allow enough tissue purchase such that the suturing device may fasten the implant to the bodily tissue.

In some embodiments, the tissue suction housing receives the suturing device through one of the suturing device openings such that the suturing device is perpendicular to the tissue suction housing.

In some embodiments, the suturing device openings each include a slot.

In some embodiments, the suturing device is a needle and the tissue suction housing receives the needle through one of the suturing device openings to pass a suture through the bodily tissue.

In some embodiments, the suturing device is a pin and the tissue suction housing receives the pin through one of the suturing device openings to pin an implant disposed on the bodily tissue to the bodily tissue. In some embodiments, the pin is biodegradable.

In some embodiments, the suturing device is a fastener.

In some embodiments, the bodily tissue is pulled up through the opening at the distal end only to the moveable member.

In some embodiments, a position of the moveable member is adjustable along an inner surface of the tissue suction housing. In some embodiments, the moveable member is fixed in the position.

In some embodiments, a distance between the opening at the distal end and the moveable member is between 2 mm and 10 mm.

In some embodiments, a distance between the opening at the distal end and one of the suturing device openings is between 2 mm and 7 mm.

In some embodiments, the medical device includes a vacuum member that is operably connected to the tissue suction housing and the vacuum member is configured to place the tissue suction housing under the vacuum. In some embodiments, the medical device further includes a tube member that connects the vacuum member to the tissue suction housing.

In some embodiments, the medical device further includes a sleeve that is disposed at the distal end of the tissue suction housing on an outer surface of the tissue suction housing and the sleeve is configured to cover the suturing device openings to place the tissue suction housing under the vacuum.

In some embodiments, the medical device further includes at least one sensor disposed on a surface of the moveable member and the sensor is configured to sense contact with the bodily tissue.

In one embodiment, a medical device includes a tissue suction housing and a moveable member disposed in the tissue suction housing. The tissue suction housing has a proximal end and a distal end. The distal end has an opening and the tissue suction housing has at least two suturing device openings. A position of the moveable member is adjustable along an inner surface of the tissue suction housing. The tissue suction housing is configured to pull up bodily tissue through the opening in the distal end when placed under a vacuum and the position of the moveable member defines a depth of penetration into the bodily tissue by a suturing device received through one of the suturing device openings.

In some embodiments, the tissue suction housing is tubular shaped.

In some embodiments, the tissue suction housing is configured to pull up the bodily tissue and an implant disposed on the bodily tissue to allow enough tissue purchase such that the suturing device may fasten the implant to the bodily tissue.

In some embodiments, the tissue suction housing receives the suturing device through one of the suturing device openings such that the suturing device is perpendicular to the tissue suction housing.

In some embodiments, the suturing device openings each include a slot.

In one embodiment, a method of suturing bodily tissue includes inserting a medical device within the body of the patient. The medical device includes a tissue suction housing having at least two suturing device openings, an opening at a distal end of the tissue suction housing and a moveable member disposed in the tissue suction housing. A vacuum is placed on the tissue suction housing to pull up the bodily tissue through the opening at the distal end of the tissue suction housing. A suturing device is inserted through one of the suturing device openings to pass a suture through the bodily tissue.

In some embodiments, the method includes moving the movable member to a position within the tissue suction housing to define a depth of penetration into the bodily tissue.

In some embodiments, the vacuum is placed on the tissue suction housing to pull up the bodily tissue and an implant disposed on the bodily tissue through the opening at the distal end of the tissue suction housing. The suturing device is inserted through one of the suturing device openings to fasten the implant to the bodily tissue.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
    a tissue suction housing having a distal end portion, the distal end portion defining an opening at a terminal end of the tissue suction housing, the opening configured to receive bodily tissue, the tissue suction housing having at least two suturing device openings; and
    a moveable member disposed in the tissue suction housing, the moveable member configured to move relatively to the distal end portion along a longitudinal axis of the distal end portion and the opening, the moveable member configured to control an amount of bodily tissue that can enter the tissue suction housing via the opening,
    wherein the tissue suction housing is configured to receive the bodily tissue through the opening in the distal end portion when placed under a vacuum and to receive a suturing device through the two suturing device openings.

2. The medical device of claim 1, wherein the tissue suction housing is tubular shaped.

3. The medical device of claim 1, wherein the tissue suction housing is configured to pull the bodily tissue and an implant disposed on the bodily tissue within the distal end portion of the tissue suction housing.

4. The medical device of claim 1, wherein the tissue suction housing is configured to receive the suturing device through the two suturing device openings such that the suturing device is positioned perpendicular to the longitudinal axis of the distal end portion of the tissue suction housing.

5. The medical device of claim 1, wherein the suturing device is a needle and the tissue suction housing is configured to receive the needle through the two suturing device openings to pass a suture through the bodily tissue.

6. The medical device of claim 1, wherein the suturing device is a pin and the tissue suction housing is configured to receive the pin through the two suturing device openings to pin an implant disposed on the bodily tissue to the bodily tissue.

7. The medical device of claim 6, wherein the pin is biodegradable.

8. The medical device of claim 1, wherein the suturing device is a fastener.

9. The medical device of claim 1, wherein the bodily tissue is pulled through the opening until reaching the moveable member.

10. The medical device of claim 1, wherein a position of the moveable member is adjustable along an inner surface of the tissue suction housing.

11. The medical device of claim 10, wherein the moveable member is configured to move towards and away from the opening.

12. The medical device of claim 1, wherein a distance between the opening and the moveable member is between 2 mm and 10 mm.

13. The medical device of claim 1, wherein a distance between the opening and one of the two suturing device openings is between 2 mm and 7 mm.

14. The medical device of claim 1, further comprising a vacuum member that is operably connected to the tissue suction housing, the vacuum member being configured to place the tissue suction housing under the vacuum.

15. The medical device of claim 14, further comprising a tube member that connects the vacuum member to the tissue suction housing.

16. The medical device of claim 1, further comprising a sleeve that is disposed on an outer surface of the distal end portion of the tissue suction housing, the sleeve being configured to cover the two suturing device openings to place the tissue suction housing under the vacuum.

17. The medical device of claim 1, further comprising at least one sensor disposed on the moveable member, the sensor being configured to sense when the moveable member contacts the bodily tissue.

18. The medical device of claim 1, wherein the tissue suction housing includes two slots.

19. A medical device, comprising:

a tissue suction housing having a distal end portion, the distal end portion defining an opening at a terminal end of the tissue suction housing, the opening configured to receive bodily tissue, the tissue suction housing having at least two suturing device openings;

a moveable member disposed in the tissue suction housing, the moveable member configured to move relatively to the distal end portion along a longitudinal axis of the distal end portion and the opening, the moveable member configured to control an amount of bodily tissue that can enter the tissue suction housing via the opening, wherein the tissue suction housing is configured to pull the bodily tissue through the opening in the distal end portion when placed under a vacuum and to receive a suturing device through the two suturing device openings; and a sleeve configured to be disposed on an outer surface of the distal end portion of the tissue suction housing, the sleeve being moveable between a first position and a second position with respect to the tissue suction housing, the sleeve configured to cover the two suturing device openings when in the first position, the sleeve configured to expose the two suturing device openings when in the second position.

* * * * *